(12) United States Patent
Blom et al.

(10) Patent No.: US 6,660,523 B2
(45) Date of Patent: Dec. 9, 2003

(54) DENDRITIC CELLS; METHODS

(75) Inventors: Bianca Blom, Uithoorn (NL); Yong-Jun Liu, Palo Alto, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/954,905

(22) Filed: Sep. 18, 2001

(65) Prior Publication Data

US 2002/0098587 A1 Jul. 25, 2002

Related U.S. Application Data

(60) Provisional application No. 60/234,142, filed on Sep. 21, 2000.

(51) Int. Cl.$^7$ .............................. C12N 5/00; C12N 5/02; C12N 5/08; C12P 21/04; A01N 63/00
(52) U.S. Cl. ..................... 435/377; 435/372; 435/325; 435/70.4; 424/93.21; 530/351
(58) Field of Search ................................ 435/377, 366, 435/70.3, 455, 70.4, 372, 325; 424/93.21, 192.1, 85.1; 514/19, 423; 536/23.4, 23.1, 23.5; 530/351

(56) References Cited

U.S. PATENT DOCUMENTS 6,472,208 B1 * 10/2002 Lemieux et al. ............ 435/325

FOREIGN PATENT DOCUMENTS

| WO | WO 99/40180 | 8/1999 |
| WO | WO 00/46349 | 8/2000 |

OTHER PUBLICATIONS

Mario Arpanati, et al., *Blood*, 95(8):2484–2490, Apr. 15, 2000. "Granulocyte–colony stimulating factor mobilizes T helper 2–inducing dendritic cells".

Jean–Francois Arrighi, et al., *Blood*, 93(7):2244–2252, Apr. 1, 1999 "Long–term culture of human CD34(+) progenitors with FLT3–ligand, thrombopoietin, and stem cell factor induces extensive amplification of a CD34(–)CD14(–) and a CD34(–)CD14(+) dendritic cell precursor".

Jacques Banchereau & Ralph M. Steinman, *Nature*, 392(6673):245–252, Mar. 19, 1998. "Dendritic cells and the control of immunity".

Ludovica Bruno, et al., *J. Exp Med*, 185(5):875–84, Mar. 3, 1997. "Identification of a committed T cell precursor population in adult human peripheral blood".

Christophe Caux, et al.,. *Blood*, 90(4):1458–1470, Aug. 15, 1997. "CD34+ hematopoietic progenitors from human cord blood differentiate along two independent dendritic cell pathways in response to granulocyte–macrophage colony–stimulating factor plus tumor necrosis factor alpha: II. Functional analysis".

Marina Cella, et al., *J. Exp. Med.*, 184(2):747–752, Aug. 1, 1996. "Ligation of CD40 on dendritic cells triggers production of high levels of interleukin–12 and enhances T cell stimulatory capacity: T–T help via APC activation".

Marina Cella, et al., *Curr. Opin. Immunol.*, 9(1):10–16, Feb. 1997. "Origin maturation and antigen presenting function of dendritic cells".

Marina Cella, et al., *Nature Medicine*, 5(8):919–923, Aug. 1999. "Plasmacytoid monocytes migrate to inflamed lymph nodes and produce large amounts of type I interferon".

Cristiana Fe d'Ostiani, et al., *J Exp Med*, 191(10):1661–1674, May 15, 2000. "Dendritic cells discriminate between yeasts and hyphae of the fungus Candida albicans. Implications for initiation of T helper cell immunity in vitro and in vivo".

Geraldine Grouard, et al., *J. Exp. Med.*, 185(6):1101–1111, Mar. 17, 1997. "The enigmatic plasmacytoid T cells develop into dendritic cells with interleukin (IL)–3 and CD40–ligand".

Akiko Iwasaki, et al., *J Exp Med*, 190(2):229–239, Jul. 19, 1999. "Freshly isolated Peyer's patch, but not spleen, dendritic cells produce interleukin 10 and induce the differentiation of T helper type 2 cells".

Noimitsu Kadowaki, et al., *J. Exp. Med.*, 192(2):219–225, Jul. 17, 2000. "Natural interferon α/β–producing cells link innate and adaptive immunity".

Pawal Kalinski, et al., *Immunol. Today*, 20(12):561–567, Dec. 1999. "T–cell priming by type–1 and type–2 polarized dendritic cells: the concept of a third signal".

Ajai Khanna, et al., *J Immunol*, 164(3):1346–54, Feb. 1, 2000. "Effects of liver–derived dendritic cell progenitors on Th1–and Th2–like cytokine responses in vitro and in vivo".

Franz Koch, et al., *J. Exp. Med.*, 184(2):741–746, Aug. 1, 1996. "High level IL–12 production by murine dendritic cells: upregulation via MHC class II and CD40 molecules and downregulation by IL–4 and IL–10".

Vadim Kronin, et al., *Int Immunol*, 9(7):1061–1064, Jul. 1997. "Are CD8+ dendritic cells (DC) veto cells? The role of CD8 on DC in DC development and in the regulation of CD4 and CD8 T cell responses".

Yong–Jun Liu & Bianca Blom, *Blood*, 95(8):2482–2483, Apr. 15, 2000. "Introduction: TH2–inducing DC2 for immunotherapy".

Roberto Maldonato–Lopez, et al., *J Exp Med*, 189(3):587–92, Feb. 1, 1999. CD8alpha+ and CD8alpha–subclasses of dendritic cells direct the development of distinct T helper cells in vivo.

(List continued on next page.)

Primary Examiner—Terry McKelvey
Assistant Examiner—M Marvich
(74) Attorney, Agent, or Firm—Edwin P. Ching; Sheela Mohan-Peterson

(57) ABSTRACT

Dendritic cell subsets, and various methods of making and using same are provided. In particular, methods for making a defined subset of dendritic cells are provided.

7 Claims, No Drawings

OTHER PUBLICATIONS

Eugene Maraskovsky, et al., *J Exp Med*, 184(5):1953–1962, Nov. 1, 1996. "Dramatic increase in the numbers of functionally mature dendritic cells in Flt3 ligand–treated mice: multiple dendritic cell subpopulations identified".

Toshiaki Ohteki, et al., *J Exp Med*, 189(12):1981–1986, Jun. 21, 1999. "Interleukin 12–dependent interferon gamma production by CD8alpha+ lymphoid dendritic cells".

Johanna Olweus, et al., *Proc Natl Acad Sci U S A*, 94(23):12551–12556, Nov. 11, 1997. "Dendritic cell ontogeny: a human dendritic cell lineage of myeloid origin".

B. Pulendran, et al., *Proc. Natl. Acad. Sci. U S A.*, 96(3):1036–1041, Feb. 2, 1999. "Distinct dendritic cell subsets differentially regulate the class of immune response in vivo".

Bali Pulendran, et al., *J Immunol*, 165(1):566–572, Jul. 1, 2000. "Flt3–ligand and granulocyte colony–stimulating factor mobilize distinct human dendritic cell subsets in vivo".

Lugui Qiu, et al., *J Hematotherapy Stem Cell Res*, 8(6):609–618, Dec. 1999. "Ex vivo expansion of CD34+ umbilical cord blood cells in a defined serum–free medium (QBSF–60) with early effect cytokines".

Caetano Reis e Sousa, et al., *Curr. Opin. Immunol.*, 11(4):392–399, Aug. 1999. "The role of dendritic cells in the induction and regulation of immunity to microbial infection".

Pieter C.M. Res, et al., *Blood*, 94(8):2647–2657, Oct. 15, 1999. "Expression of pTalpha mRNA in a committed dendritic cell precursor in the human thymus".

P. Reusser, *Schweiz Med Wochenschr*, 130(4):101–112, Jan. 29, 2000. "Antiviral therapy: current options and challenges".

Marie–Clotilde Rissoan, et al., *Science*, 283(5405):1183–1186, Feb. 19, 1999. "Reciprocal control of T helper cell and dendritic cell differentiation".

Federica Sallusto and Antonio Lanzavecchia, *J Exp Med*, 189(4):611–614, Feb. 15, 1999. "Mobilizing dendritic cells for tolerance, priming, and chronic inflammation".

Taizo Shimomura, et al., *Int J Hematol*, 71(1):33–39, Jan. 2000. "Thrombopoietin stimulates murine lineage negative, Sca–1+, C–Kit+, CD34–cells: comparative study with stem cell factor or interleukin–3".

Ken Shortman, *Immuno.l Cell. Biol.*, 78(2):161–165, Apr. 2000. "Dendritic cells: multiple subtypes, multiple origins, multiple functions".

Ken Shortman, et al., *Immunological Reviews*, 78(2):161–165, Apr. 2000. "The linkage between T–cell and dendritic cell development in mouse thymus".

Michael R. Shurin, et al., *Cytokine Growth Factor Rev*, 9(1):37–48, Mar. 1998. "FLT3: receptor and ligand. Biology and potential clinical application".

Frederick P. Siegal, et al., *Science*, 284(5421):1835–1837, Jun. 11, 1999. "The nature of the principal type 1 interferon–producing cells in human blood".

Philip A. Stumbles, et al., *J. Exp Med*, 188(11):2019–2031, Dec. 7, 1998. "Resting respiratory tract dendritic cells preferentially stimulate T helper cell type 2 (Th2) responses and require obligatory cytokine signals for induction of Th1 immunity".

A.W. Thompson, et al., *J Leukoc Biol*, 66(2):322–330, Aug. 1999. "Hepatic dendritic cells: immunobiology and role in liver transplantation".

H. Vallin, et al., *Clin Exp Immunol*, 115(1):196–202, Jan. 1999. "Patients with systemic lupus erythematosus (SLE) have a circulating inducer of interferon–alpha (IFN–alpha) production acting on leucocytes resembling immature dentritic cells".

* cited by examiner

DENDRITIC CELLS; METHODS

This application claims benefit of U.S. Provisional Patent Application No. 60/234,142, filed Sep. 21, 2000.

FIELD OF THE INVENTION

The invention relates generally to methods of making and using certain defined subsets of dendritic cells, more particularly, to methods of in vitro production of a subset of dendritic cells which produce large amounts of interferon.

BACKGROUND

The circulating component of the mammalian circulatory system comprises various cell types, including red and white blood cells of the erythroid and myeloid cell lineages. See, e.g., Rapaport (1987) *Introduction to Hematology* (2d ed.) Lippincott, Philadelphia, Pa.; Jandl (1987) *Blood: Textbook of Hematology*, Little, Brown and Co., Boston, Mass.; and Paul (ed. 1993) *Fundamental Immunology* (3d ed.) Raven Press, N.Y.

Dendritic cells (DCs) are the most potent of antigen-presenting cells. See, e.g., Paul (ed. 1993) *Fundamental Immunology* 3d ed., Raven Press, NY. Antigen presentation refers to the cellular events in which a proteinaceous antigen is taken up, processed by antigen presenting cells (APC), and then recognized to initiate an immune response. The most active antigen presenting cells have been characterized as the macrophages (which are direct developmental products from monocytes), dendritic cells, and certain B cells. DCs are highly responsive to inflammatory stimuli such as bacterial lipopolysaccharides (LPS) and cytokines such as tumor necrosis factor alpha (TNFα). The presence of cytokines and LPS can induce a series of phenotypic and functional changes in DC that are collectively referred to as maturation. See, e.g., Banchereau and Schmitt *Dendritic Cells in Fundamental and Clinical Immunology* Plenum Press, NY.

Dendritic cells can be classified into various categories, including: interstitial dendritic cells of the heart, kidney, gut, and lung; Langerhans cells in the skin and mucous membranes; interdigitating dendritic cells in the thymic medulla and secondary lymphoid tissue; and blood and lymph dendritic cells. Although dendritic cells in each of these compartments are CD45+ leukocytes that apparently arise from bone marrow, they may exhibit differences that relate to maturation state and microenvironment. Maturational changes in DCs include, e.g., silencing of antigen uptake by endocytosis, upregulation of surface molecules related to T cell activation, and active production of a number of cytokines including TNFα and IL-12. Upon local accumulation of TNFα, DCs migrate to the T cell areas of secondary lymphoid organs to activate antigen specific T cells.

Many factors have been identified which influence the differentiation process of precursor cells, or regulate the physiology or migration properties of specific cell types. See, e.g., Mire-Sluis and Thorpe (1998) *Cytokines* Academic Press, San Diego; Thomson (ed. 1998) *The Cytokine Handbook* (3d ed.) Academic Press, San Diego; Metcalf and Nicola (1995) *The Hematopoietic Colony Stimulating Factors* Cambridge University Press; and Aggarwal and Gutterman (1991) *Human Cytokines* Blackwell. These factors provide yet unrecognized biological activities, e.g., on different untested cell types.

However, dendritic cells are poorly characterized, both in terms of responses to soluble factors, and many of their functions and mechanisms of action. The absence of knowledge about the physiological properties and responses of these cells limits their understanding. Thus, medical conditions where regulation, development, or physiology of dendritic cells is unusual remain unmanageable. The present invention addresses these issues.

SUMMARY OF THE INVENTION

The present invention is based, in part, upon the surprising discovery of conditions which result in large numbers of viable type I IFN producing cells, or pDC2 cells. The invention provides methods comprising contacting $CD34^{++}$ $CD45RA^-$ early haematopoietic progenitor cells with an effective amount of FLT3 ligand ex vivo, thereby inducing differentiation of the cells to IFN producing DC. Typically, the effective amount is at least 70 ng/ml; the contacting is for at least 15 days; the IFN producing DC produce at least 5000 pg IFN per 20,000 cells over 24 h after viral stimulation; the early progenitor cells expand at least about 10 fold; and/or the IFN producing cells number at least 2.5 million. In a preferred embodiment, the contacting is with TPO, and the early progenitor cells expand at least 30 fold. In other embodiments, the early progenitor cells expand at least 100 fold; or after the expansion, at least 3% of the resulting cell culture is IFN producing DC; or the IFN producing DC accumulate in 24 h at least 40,000 pg IFN per 20,000 cells after viral stimulation.

In other embodiments, the invention provides methods of producing IPC comprising contacting IPC precursors with an effective amount of a combination of both FLT3 Ligand and TPO. Preferably, the contacting is for at least 13 days; the precursors are $CD34^{++}CD45RA^-$ early haematopoietic progenitor cells; the IPC accumulate in 24 h at least 5000 pg IFN per 20,000 IPC after viral stimulation; and/or the IPC number at least $1\times10^7$ cells. Typically, the contacting is ex vivo.

In yet another embodiment, the invention provides populations of at least $3\times10^6$ viable IPC derived from a single individual, e.g., at least 7, 10, or $15\times10^6$ cells. Preferably, cells are cultured in the presence of both FLT3 Ligand and TPO to produce the IPC, e.g., in vitro for at least 14 days where the FLT3 ligand is at least 70 ng/ml; and/or the TPO is at least 70 ng/ml. Typically, the IPC are $CD34^-CD45RA^{++}$ $CD4^+IL-3R\alpha^{++}$ cells.

DETAILED DESCRIPTION OF THE INVENTION

Outline
I. General
   A. IPC
   B. Developmental pathway
II. Producing IPC
   A. FLT3 Ligand
   B. thrombopoietin (TPO)
   C. Other Molecules
III. Uses
I. General Natural Interferon-α producing cells (IPC) are key effector cells in anti-viral innate immunity. These cells produce up to 1000 times more IFN-α than other blood cell types in response to viral stimulation. IPCs also have the capacity to become dendritic cells, which are key antigen presenting cells in the induction of T cell mediate immune responses.

Upon viral stimulation, the natural IFN-α/β producing cells (IPCs, also known as pre-DC2) in human blood and peripheral lymphoid tissues rapidly produce very large amounts of IFN-α/β. After performing this innate anti-viral immune response, IPCs can differentiate into dendritic cells and strongly stimulate T cell mediated adaptive immune responses. Using four-color immunofluorescence flow cytometry, the developmental pathway has been mapped herein to pre-DC2/IPCs from $CD34^+$ heamatopoietic stem cells in human fetal liver, bone marrow, and cord blood. At least four developmental stages have been identified, including $CD34^{++}CD45RA^-$ early progenitor cells, $CD34^{++}CD45RA^+$ late progenitor cells, $CD34^+CD45RA^{++}CD4^+IL-3R\alpha^{++}$pro-DC2, and $CD34^-CD45RA^{++}CD4^+IL-3R\alpha^{++}$ pre-DC2/IPCs. Pro-DC2s already have acquired the capacity to produce large amounts of IFN-$\alpha$/$\beta$ upon viral stimulation and to differentiate into DCs in culture with IL-3 and CD40-Ligand. The expression of pre-T cell receptor (TCR) alpha chain mRNA by both pro-DC2 and pre-DC2 supports the lymphoid origin of the pre-DC2/IPC lineage. $CD34^{++}CD45RA^-$ early progenitor cells did not have the capacity to produce large amounts of IFN-$\alpha$/$\beta$ in response to viral stimulation, however they can be induced to undergo clonal expansion and differentiation into IPCs/Pre-DC2 in culture with FLT3-Ligand.

Dendritic cells (DCs) represent heterogeneous populations of heamatopoietic-derived cells that display potent ability to induce primary T cell activation, polarization, and in certain circumstances tolerance. See Sousa, et al. (1999) *Curr. Op. Immunol.* 11:392–399; Sallusto and Lanzavecchia (1999) *J. Exp. Med.* 189:611–614; Banchereau and Steinman (1998) *Nature* 392:245–252; Cella, et al. (1997) *Curr. Opin. Immunol.* 9:10–16; and Steinman (1991) *Annu. Rev. Immunol.* 9:271–296. The distinct capacity of DCs to induce immunity versus tolerance or Th1 versus Th2 responses depends on their maturation stage (Cella, et al. (1997) *Curr. Opin. Immunol.* 9:10–16; and Kalinski, et al. (1999) *Immunol. Today* 20:561–567), signals that induce or inhibit DC maturation (Cella, et al. (1997) *Curr. Opin. Immunol.* 9:10–16; and Kalinski, et al. (1999) *Immunol. Today* 20:561–567; d'Ostiani, et al. (2000) *J. Exp. Med.* 191:1661–1674), as well as the lineage origin of DCs (Pulendran, et al. (1999) *Proc. Nat'l Acad. Sci. USA* 96:1036–1041; Reis e Sousa, et al. (1999) *Curr. Opin. Immunol.* 11:392–399; Maldonado-Lopez, et al. (1999) *J. Exp. Med.* 189:587–592; Arpinati, et al. (2000) *Blood* 95:2484–2490; Liu and Blom (2000) *Blood* 95:2482–2483; and Shortman (2000) *Immunol. Cell Biol.* 78:161–165). A lymphoid DC developmental pathway was suggested by the finding that mouse thymic lymphoid precursors can give rise to both T cells and $CD8^+CD11b^-$ DCs. Ardavin, et al. (1993) *Nature* 362:761–763; and Shortman, et al. (1998) *Immunol. Rev* 165:39–46. In addition, a well-established myeloid DC pathway giving rise to $CD8^-CD11b^+$ DCs has been defined. Inaba, et al. (1992) *J. Exp. Med.* 176:1693–1702; Inaba, et al. (1993) *Proc. Nat'l Acad. Sci. USA* 90:3038–2042; and Young and Steinman (1996) *Stem Cells* 14:376–287. Recent studies suggest that $CD8^+CD11\ b^-$ lymphoid DCs and $CD8^-CD11b^+$ myeloid DCs may have different functions in T cell activation/tolerance or Th1/Th2 differentiation. Pulendran, et al. (1999) *Proc. Nat'l Acad. Sci. USA* 96:1036–1041; Maldonado-Lopez, et al. (1999) *J. Exp. Med.* 189:587–592; Suss and Shortman (1996) *J. Exp. Med.* 183:1789–1796; Kronin, et al. (1997) *Int. Immunol.* 9:1061–1064; Stumbles, et al. (1998) *J. Exp. Med.* 188:2019–2031; Ohteki, et al. (1999) *J. Exp. Med.* 189:1981–1986; Thomson, et al. (1999) *J. Leukoc. Biol.* 66:322–330; Iwasaki and Kelsall (1999) *J. Exp. Med.* 190:229–239; and Khanna, et al. (2000) *J. Immunol.* 164:1346–1354.

In humans, two distinct populations of dendritic cell precursors have been identified in the blood. Monocytes (pre-DC1), which belong to the myeloid lineage, differentiate into immature DC1 after 5 days of culture in granulocyte colony-stimulating factor (GM-CSF) and IL-4. Sallusto and Lanzavecchia (1994) *J. Exp. Med.* 179:1109–1118; and Romani, et al. (1994) *J. Exp. Med.* 180:83–93. Upon CD40-Ligand activation, immature myeloid DC1 undergo maturation and produce large amounts of IL-12. Cella, et al. (1996) *J. Exp. Med.* 184:747–752; and Koch, et al. (1996) *J. Exp. Med.* 184:741–746. The mature DC1 induced by CD40-Ligand are able to polarize naive $CD4^+$ T cells into Th1 cells. Rissoan, et al. (1999) *Science* 283:1183–1186. The second type of DC precursor cells, pre-DC2 (previously known as plasmacytoid T/monocytes) are characterized by a unique surface phenotype ($CD4^+IL-3R\alpha^{++}CD45RA^+HLA-DR^+$ lineage markers$^-$ and $CD11c^-$), and at the ultrastructural level resemble immunoglobulin-secreting plasma cells. Grouard, et al. (1997) *J. Exp. Med.* 185:1101–1111; and Facchetti, et al. (1999) *Histopathology* 35:88–89. Several lines of evidence suggest that pre-DC2s are of lymphoid origin: i) pre-DC2 lack expression of the myeloid antigens CD11c, CD13, CD33, and mannose receptor (Grouard, et al. (1997) *J. Exp. Med.* 185:1101–1111; and Res, et al. (1999) *Blood* 94:2647–2657), ii) pre-DC2 isolated from the thymus, express the lymphoid markers CD2, CD5, and CD7 (Res, et al. (1999) *Blood* 94:2647–2657), iii) pre-DC2 have little phagocytic activity (Grouard, et al. (1997) *J. Exp. Med.* 185:1101–1111), iv) pre-DC2 do not differentiate into macrophages following culture with GM-CSF and macrophage-colony stimulating factor (M-CSF) (Grouard, et al. (1997) *J. Exp. Med.* 185:1101–1111), v) pre-DC2 express pre-TCR alpha transcripts (Res, et al. (1999) *Blood* 94:2647–2657; and Bruno, et al. (1997) *J. Exp. Med.* 185:875–884), and vi) development of pre-DC2, T and B cells, but not myeloid DC is blocked by ectopic expression of inhibitor of DNA binding (Id)2 or Id3. Pre-DC2 differentiate into immature DC2 when cultured with monocyte conditional medium (O'Doherty, et al. (1994) *Immunology* 82:487–493), IL-3 (Rissoan, et al. (1999) *Science* 283:1183–1186; Grouard, et al. (1997) *J. Exp. Med.* 185:1101–1111; and Olweus, et al. (1997) *Proc. Nat'l Acad. Sci. USA* 94:12551–12556), IFN-$\alpha$/$\beta$ and tumor necrosis factor (TNF)-$\alpha$ or viruses, like Herpes Simplex Virus or Influenza virus (Kadowaki, et al. (2000) *J. Exp. Med.* 192:219–226). Upon CD40-Ligand activation, immature DC2 undergo maturation (Grouard, et al. (1997) *J. Exp. Med.* 185:1101–1111), but produce only low levels of IL-12 (Rissoan, et al. (1999) *Science* 283:1183–1186). Mature DC2 are able to polarize naïve $CD4^+$ T cells into a Th2 phenotype (Arpinati, et al. (2000) *Blood* 95:2484–2490; and Rissoan, et al. (1999) *Science* 283:1183–1186). Recent studies showed that the pre-DC2 are the elusive natural interferon producing cells (IPC), capable of producing high amounts of IFN-$\alpha$/$\beta$ upon viral stimulation (Siegal, et al. (1999) *Science* 284:1835–1837; and Cella, et al. (1999) *Nature Med.* 5:919–923). Taken together, pre-DC2/IPCs represent a unique heamatopoietic lineage, capable of performing crucial functions both in innate and in adapted immunity.

The pathway underlying the development of pre-DC2/IPC from $CD34^+$ heamatopoietic stem cells has not been elucidated. Caux, et al. (1997) *Blood* 90:1458–1470 showed that cord blood $CD34^+$ heamatopoietic progenitor cells cultured in GM-CSF, stem cell factor (SCF), and TNF-$\alpha$ differentiate along two DC pathways: i) the Langerhans cell (LC) pathway, in which intermediate $CD14^-CD1a^+$ DC precursors differentiated into LCs characterized by the expression of CD1a, Birbeck granules, the Lag antigen, and E cadherin; and ii) the dermal DC pathway, in which intermediate $CD14^+CD1a^-$ DC precursors differentiate into dermal DCs characterized by the expression of CD1a, CD9, CD68, CD2, and factor XIIIa (Caux, et al. (1996) *J. Exp. Med.* 184:695–706). Recently, a common human lymphoid progenitor (CLP) in the bone marrow was described that expresses both CD45RA and CD10. Galy, et al. (1995) *Immunity* 3:459–473. These cells develop into T, B, NK cells, and DC, but not into erythroid, megakaryocytic, and myeloid cells. In these experiments, exclusively $CD1a^+$ LCs were generated with a cocktail of 9 cytokines (IL-1, IL-3, IL-6, IL-7, SCF, GM-CSF, TNF, erythropoietin (EPO), and FLT3-Ligand). Of these cytokines, the heamatopoietic growth factor FLT3-Ligand has been shown to play an important role in the proliferation, survival, and differentiation of early murine and human heamatopoietic precursor cells. Zeigler, et al. (1994) *Blood* 84:2422–2430; and Shurin, et al. (1998) *Cytokine Growth Factor Rev.* 9:37–48. Interestingly, volunteer donors injected with FLT3-Ligand had a 13-fold increase in pre-DC2 number and a 48-fold increase in $CD11c^+$ myeloid DC number in the blood stream. Pulendran, et al. (2000) *J. Immunol.* 165:566–572. Consistent with this finding, injection of mice with human FLT3-Ligand led to dramatically increased numbers of both myeloid and lymphoid DC not only in the peripheral blood, but also in the bone marrow, thymus, and secondary lymphoid tissues. Pulendran, et al. (1999) *Proc. Nat'l Acad. Sci. USA* 96:1036–1041; Maldonado-Lopez, et al. (1999) *J. Exp. Med.* 189:587–592; Maraskovsky, et al. (1996) *J. Exp. Med.* 184:1953–1962; and Pulendran, et al. (1997) *J. Immunol.* 159:2222–2231. Two recent reports revealed a 5 to 6-fold increase in pre-DC2/IPC numbers in the blood of granulocyte-colony stimulating factor (G-CSF) treated donors. Arpinati, et al. (2000) *Blood* 95:2484–2490; and Pulendran, et al. (2000) *J. Immunol.* 165:566–572. It is not clear from these studies, however, whether FLT3-Ligand and G-CSF enhance the differentiation of pre-DC2 from heamatopoietic progenitor cells, or promote the migration of pre-DC2 from bone marrow into blood.

The aims of the current studies are: i) to trace the developmental pathway of pre-DC2/IPCs from $CD34^{++}$ heamatopoietic progenitor cells; and ii) to identify the stimuli that can induce $CD34^{++}$ heamatopoietic progenitor cells to differentiate into pre-DC2/IPCs.

Herein is described the identification of CD34-expressing precursors of pre-DC2/IPCs from human fetal tissues and cord blood. In addition, the generation of pre-DC2/IPCs from early heamatopoietic stem cells in vitro cultures is described.

II. Producing IPC

Various aspects of the IPCs have been described, e.g., in Kadowaki, et al. (2000) *J. Expt'l Med.* 19:219–226; Rissoan, et al. (1999) *Science* 283:1183–1186; and Grouard, et al. (1997) *J. Exp. Med.* 185:1101–1111. The IFN-α production assays are described below, but can be immunoassays after viral induction. An appropriate virus is selected, e.g., HSV-1, KOS strain, attenuated by γ-irradiation, to infect the cell cultures. Typical multiplicity of infection numbers are 1, 3, 5, 7, 10, 13, 17, or 20 pfu/cell. The amount of IFN-α produced is determined after accumulation for a defined period of time, e.g., 12, 18, 24, or 36 h. The amounts of IFN produced will vary according to individual and other parameters, but will be at least about 5000 pg IFN per 20,000 cells accumulated over 24 h, but will preferably be more, e.g., 10, 20, 30, 40, 50, 60, or 70 thousand, or more.

DC precurser populations may originate from various sources, e.g., fetal liver, cord blood, bone marrow, or G-CSF mobilized blood. From adults, bone marrow derived precursors may be derived from biopsy or fresh cadaver samples. G-CSF mobilization may use appropriate amounts of cytokine, without or with FLT3 ligand. See, e.g., Mire-Sluis and Thorpe (1998) *Cytokines* Academic Press, San Diego; Thomson (ed. 1998) *The Cytokine Handbook* (3d ed.) Academic Press, San Diego; Metcalf and Nicola (1995) *The Hematopoietic Colony Stimulating Factors* Cambridge University Press; Aggarwal and Gutterman (1991) *Human Cytokines* Blackwell; WO97/12633; and WO99/26639. After mobilization, precursors may be isolated, e.g., by leukophoresis, and used in methods analogous to those described.

Isolation of these IPCs is inefficient from natural sources due, in part, to their rarity. Though small numbers can be isolated from natural sources, they are very fragile and not easily culturable to provide viable cells. Moreover, there are limitations on amounts of material that can be harvested from a single individual. The cells cannot be stored to remain viable to allow multiple isolations from a single individual to be pooled. However, the present methods allow for the proliferation and expansion of precursors to provide larger numbers of the cells from a single individual. In vitro methods using FLT3 Ligand are provided, and combinations of FLT3 Ligand with TPO provide even larger numbers of IPCs.

DC precursors are cultured under appropriate conditions, e.g., in various cytokines to induce proliferation and sustain development. Many combinations of cytokines among FLT-3 Ligand, SCF, IL-7, IL-3, G-CSF, and GM-CSF can inhibit development, and/or fail to support cell proliferation. FLT-3 Ligand sustains the combination of both proliferation and differentiation. In combination with thrombopoietin (TPO; Shimomura, et al. (2000) *Int. J. Hematol.* 71:33–39; and Qiu, et al. (1999) *J. Hematother. Stem Cell Res.* 8:609–618), FLT3 Ligand has a dramatic effect on both proliferation and maintenance of differentiation of DC populations. The length of time and amounts of cytokines for such proliferation and development are routinely optimized. Under the conditions described herein, the time of contacting precursors with cytokine is from at least about 7, 10, 13, 15, 17, 19, 21, 23, 25, or 27 days. The appearance of the pDC2 cells occurs over those time periods, and the proportion of cells is in the range from 4, 6, 8, or 10% or more. The amounts of cytokine used had been optimized around, for IL-3 10 ng/ml; for GM-CSF 800 U/ml; for FLT-3 Ligand 100 ng/ml; for TPO 100 ng/ml; for SCF 10 ng/ml; for IL-7 10 ng/ml; and for G-CSF 5 ng/ml. However, these may be titrated, and should have similar effects to the respective cytokine at amounts of, e.g., 30%, 50%, 70%, 90%, 110%, 130%, etc. The appearance of the pDC2, under the described conditions, typically begins at about 11 days and increases at 13, 15, 17, 19, 21, and 23 days. The numbers of the cells seem to peak at about 25–28 days. Viability of cells may decrease thereafter, or the cells may further differentiate or lose their differentation markers.

The conditions evaluated herein are directed primarily to in vitro cultures, but the periods for in vivo treatment should be comparable or perhaps even shorter periods of time, e.g., by 50%, 60%, 70%, 80%, 90%, or so.

Conversely, it would be expected that the differentiation of pDC2 may be blocked by blocking the signals mediated by the indicated cytokines. Thus, antagonists of FLT3 Ligand and/or TPO may be administered in critical windows or longer term to block the differentiation of these cells. Thus, in circumstances where IPC normally produce IFN, antagonists may lower the systemic or local IFN levels.

Recombinant or other sources of the cytokines are known, and can be administered in culture or in vivo as appropriate.

Recombinant protein can be expressed and purified in eukaryotic or prokaryotic cells as described, e.g., in Coligan, et al. (eds. 1995 and periodic supplements) *Current Protocols in Protein Science* John Wiley & Sons, New York, N.Y.; and Ausubel, et al (eds. 1987 and periodic supplements) *Current Protocols in Molecular Biology,* Greene/Wiley, New York, N.Y.

Alternatively, antagonists are available, e.g., antibodies to ligands, soluble receptors, mutein antagonists, etc. Naturally folded or denatured material, perhaps expressed on cell surfaces, can be used, as appropriate, for producing antibodies. Either monoclonal or polyclonal antibodies may be generated, e.g., for subsequent use in immunopurification methods.

III. Uses

IPC will be important in a number of therapeutic and research applications. See, e.g., Kadowaki, et al. (2000) *J. Expt'l Med.* 192:219–226; and Liu and Blom (2000) *Blood* 95:2482–2483. They will be used in cellular therapy for viral infections and diseases, e.g., HIV or hepatitis. The cells will produce natural interferons, and can substitute for administration of the interferons in treatment of medical conditions. The cells may be produced in vivo or ex vivo according to methods described. These methods also provide means to isolate large quantities of pDC2 cells, which will allow for further study and characterization. These cells will be useful in studying the molecular mechanisms regulating IFN-α production.

In contrast, there will be circumstances where the generation of pDC2 cell types may be counter indicated. Prevention of such differentiation may be effected by blockage of signaling mediated by the respective differentiation factors. This may take the forms of mutein antagonists, antibody antagonists, receptor antibody antagonists, soluble receptor constructs, small molecule antagonists, etc. Such may be indicated where high levels of IFN are deleterious, e.g., in autoimmune contexts such as lupus (see, e.g., Vallin, et al. (1999) *Clin. Exp. Immunol.* 115:196–202; Schilling, et al. (1991) *Cancer* 68:1536–1537), or in tumor contexts.

So, the present invention provides means to produce and purify desired dendritic cell subsets, or alternatively to block such. Alternatively, labeling can be used to FACS sort cells which specifically express these markers. Populations of substantially homogeneous IPCs will have important utility in research or therapeutic environments.

Effects on various cell types may be indirect, as well as direct. A statistically significant change in the numbers of cells will typically be at least about 10%, preferably 20%, 30%, 50%, 70%, 90%, or more. Effects of greater than 100%, e.g., 130%, 150%, 2×, 3×, 5×, etc., will often be desired. The effects may be specific in numbers or proportions of the various cell subpopulations.

The present invention will be useful in the treatment of medical conditions or diseases associated with innate or viral immunity. See, e.g., Frank, et al. (eds. 1995) *Samter's Immunologic Diseases,* 5th Ed., vols. I–II, Little, Brown and Co., Boston, Mass.

The cells or cytokines described may be combined with other treatments of the medical conditions described herein, e.g., an antibiotic, antifungal, antiviral, immune suppressive therapeutic, immune adjuvant, analgesic, anti-inflammatory drug, growth factor, cytokine, vasodilator, or vasoconstrictor. See, e.g, the Physician's Desk Reference, both prescription and non-prescription compendiums. Preferred combination therapies include the cells or reagents with various anti-infective agents.

Standard immunological techniques are described, e.g., in Hertzenberg, et al. (eds. 1996) *Weir's Handbook of Experimental Immunology* vols. 1–4, Blackwell Science; Coligan (1991) *Current Protocols in Immunology* Wiley/Greene, N.Y.; and *Methods in Enzymology* volumes 70, 73, 74, 84, 92, 93, 108, 116, 121, 132, 150, 162, and 163. These will allow use of the reagents for purifying cell subpopulations, etc.

To prepare pharmaceutical or sterile compositions including, e.g., TPO, the material is admixed with a pharmaceutically acceptable carrier or excipient which is preferably inert. Preparation of such pharmaceutical compositions is known in the art, see, e.g., *Remington's Pharmaceutical Sciences* and *U.S. Pharmacopeia: National Formulary,* Mack Publishing Company, Easton, Pa. (1984). Typically, therapeutic compositions are sterile. Alternatively, FLT3 Ligand and/or TPO antagonist compositions can be prepared.

Agonists, e.g., natural ligand, or antagonists, e.g., antibodies or binding compositions, are normally administered parenterally, preferably intravenously. Since such protein or peptide antagonists may be immunogenic they are preferably administered slowly, either by a conventional IV administration set or from a subcutaneous depot, e.g. as taught by Tomasi, et al., U.S. Pat. No. 4,732,863.

When administered parenterally the therapeutics will typically be formulated in a unit dosage injectable form (solution, suspension, emulsion) in association with a pharmaceutically acceptable parenteral vehicle. Such vehicles are inherently nontoxic and nontherapeutic. The antagonist may be administered in aqueous vehicles such as water, saline, or buffered vehicles with or without various additives and/or diluting agents. Alternatively, a suspension, such as a zinc suspension, can be prepared to include the peptide. Such a suspension can be useful for subcutaneous (SQ), intradermal (ID), or intramuscular (IM) injection. The proportion of therapeutic entity and additive can be varied over a broad range so long as both are present in effective combination amounts. The therapeutic is preferably formulated in purified form substantially free of aggregates, other proteins, endotoxins, and the like, at concentrations of about 5 to 30 mg/ml, preferably 10 to 20 mg/ml. Preferably, the endotoxin levels are less than 2.5 EU/ml. See, e.g., Avis, et al. (eds. 1993) *Pharmaceutical Dosage Forms: Parenteral Medications* 2d ed., Dekker, NY; Lieberman, et al. (eds. 1990) *Pharmaceutical Dosage Forms: Tablets* 2d ed., Dekker, NY; Lieberman, et al. (eds. 1990) *Pharmaceutical Dosage Forms: Disperse Systems* Dekker, NY; Fodor, et al. (1991) *Science* 251:767–773; Coligan (ed.) *Current Protocols in Immunology;* Hood, et al. *Immunology* Benjamin/Cummings; Paul (ed. 1997) *Fundamental Immunology* 4th ed., Academic Press; Parce, et al. (1989) *Science* 246:243–247; Owicki, et al. (1990) *Proc. Nat'l Acad. Sci. USA* 87:4007–4011; and Blundell and Johnson (1976) *Protein Crystallography,* Academic Press, New York.

Selecting an administration regimen for a therapeutic agonist or antagonist depends on several factors, including the serum or tissue turnover rate of the therapeutic, the immunogenicity of the therapeutic, or the accessibility of the target cells. Preferably, an administration regimen maximizes the amount of therapeutic delivered to the patient consistent with an acceptable level of side effects. Accordingly, the amount of therapeutic delivered depends in part on the particular agonist or antagonist and the severity of the condition being treated. Guidance in selecting appropriate doses of antibodies is found in the literature on therapeutic uses, e.g. Bach et al., chapter 22, in Ferrone, et al. (eds. 1985) *Handbook of Monoclonal Antibodies* Noges Publications, Park Ridge, N.J.; and Russell, pgs. 303–357, and Smith, et al., pgs. 365–389, in Haber, et al. (eds. 1977) *Antibodies in Human Diagnosis and Therapy* Raven Press, New York, N.Y.

Determination of the appropriate dose is made by the clinician, e.g., using parameters or factors known in the art to affect treatment or predicted to affect treatment. Generally, the dose begins with an amount somewhat less than the optimum dose and it is increased by small increments thereafter until the desired or optimum effect is achieved relative to any negative side effects. Numbers of pDC2 cells in defined samples might be important indicators of when an effective dose is reached. Preferably, an antibody or binding composition thereof that will be used is derived from the same species as the animal targeted for treatment, thereby minimizing a humoral response to the reagent.

The total weekly dose ranges for antibodies or fragments thereof, which specifically bind to cytokine, range generally from about 1 ng, more generally from about 10 ng, typically from about 100 ng; more typically from about 1 µg, more typically from about 10 µg, preferably from about 100 µg, and more preferably from about 1 mg per kilogram body weight. Although higher amounts may be more efficacious, the lower doses typically will have fewer adverse effects. Generally the range will be less than 100 mg, preferably less than about 50 mg, and more preferably less than about 25 mg per kilogram body weight.

The weekly dose ranges for antagonists, e.g., antibody, binding fragments, range from about 10 µg, preferably at least about 50 µg, and more preferably at least about 100 µg per kilogram of body weight. Generally, the range will be less than about 1000 µg, preferably less than about 500 µg, and more preferably less than about 100 µg per kilogram of body weight. Dosages are on a schedule which effects the desired treatment and can be periodic over shorter or longer term. In general, ranges will be from at least about 10 µg to about 50 mg, preferably about 100 µg to about 10 mg per kilogram body weight.

Other antagonists of the ligands, e.g., muteins, are also contemplated. Hourly dose ranges for muteins range from at least about 10 µg, generally at least about 50 µg, typically at least about 100 µg, and preferably at least about 500 µg per hour. Generally the dosage will be less than about 100 mg, typically less than about 30 mg, preferably less than about 10 mg, and more preferably less than about 6 mg per hour. General ranges will be from at least about 1 µg to about 1000 µg, preferably about 10 µg to about 500 µg per hour.

The phrase "effective amount" means an amount sufficient to effect a desired response, or to ameliorate a symptom or sign of the target condition. Typical mammalian hosts will include mice, rats, cats, dogs, and primates, including humans. An effective amount for a particular patient may vary depending on factors such as the condition being treated, the overall health of the patient, the method, route, and dose of administration and the severity of side affects. Preferably, the effect will result in a change in quantitation of at least about 10%, preferably at least 20%, 30%, 50%, 70%, or even 90% or more. When in combination, an effective amount is in ratio to a combination of components and the effect is not necessarily limited to individual components alone.

An effective amount of therapeutic will modulate the symptoms typically by at least about 10%; usually by at least about 20%; preferably at least about 30%; or more preferably at least about 50%. Such will result in, e.g., statistically significant and quantifiable changes in the numbers of cells being affected. This may be an increase or decrease in the numbers of target cells appearing within a time period or target area.

The present invention provides reagents which will find use in therapeutic applications as described elsewhere herein. See, e.g., Berkow (ed.) *The Merck Manual of Diagnosis and Therapy,* Merck & Co., Rahway, N.J.; Thorn, et al. *Harrison's Principles of Internal Medicine,* McGraw-Hill, N.Y.; Gilman, et al. (eds. 1990) *Goodman and Gilman's: The Pharmacological Bases of Therapeutics.* 8th Ed., Pergamon Press; *Remington's Pharmaceutical Sciences.* 17th ed. (1990), Mack Publishing Co., Easton, Pa.; Langer (1990) *Science* 249:1527–1533; and *Merck Index,* Merck & Co., Rahway, N.J.

Antibodies to marker proteins may be used for the identification or sorting of cell populations expressing those markers. Methods to sort such populations are well known in the art, see, e.g., Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

Moreover, antisense nucleic acids may be used. For example, antisense polynucleotides against the ligand encoding nucleic acids may function in a manner like ligand antagonists, and antisense against the receptor may function like receptor antagonists. Thus, it may be possible to block the signaling through the pathway with antisense nucleic acids. Conversely, nucleic acids for the receptor may serve as agonists, increasing the numbers of receptor on the cell, thereby increasing cell sensitivity to ligand, and perhaps blocking the normal apoptotic signal described.

The broad scope of this invention is best understood with reference to the following examples, which are not intended to limit the inventions to the specific embodiments.

EXAMPLES

I. General Methods

Some of the standard methods are described or referenced, e.g., in Maniatis, et al. (1982) *Molecular Cloning, A Laboratory Manual,* Cold Spring Harbor Laboratory, Cold Spring Harbor Press; Sambrook, et al. (1989) *Molecular Cloning: A Laboratory Manual,* (2d ed.), vols. 1–3, CSH Press, NY; Ausubel, et al., *Biology,* Greene Publishing Associates, Brooklyn, N.Y.; or Ausubel, et al. (1987 and Supplements) *Current Protocols in Molecular Biology,* Greene/Wiley, New York; Innis, et al. (eds.)(1990) *PCR Protocols: A Guide to Methods and Applications* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology,* vol. 182, and other volumes in this series; manufacturer's literature on use of protein purification products, e.g., Pharmacia, Piscataway, N.J., or Bio-Rad, Richmond, Calif.; and Coligan, et al. (eds.) (1995 and periodic supplements) *Current Protocols in Protein Science,* John Wiley & Sons, New York, N.Y. Combination with recombinant techniques allow fusion to appropriate segments, e.g., to a FLAG sequence or an equivalent which can be fused via a protease-removable sequence. See, e.g., Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *QIAexpress: The High Level Expression & Protein Purification System* QIAGEN, Inc., Chatsworth, Calif.

Standard immunological techniques are described, e.g., in Hertzenberg, et al. (eds. 1996) *Weir's Handbook of Experimental Immunology* vols. 1–4, Blackwell Science; Coligan (1991) *Current Protocols in Immunology* Wiley/Greene, N.Y.; and *Methods in Enzymology* volumes. 70, 73, 74, 84, 92, 93, 108, 116, 121, 132, 150, 162, and 163.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Flow Cytometric Analysis and Cell Sorting of Human Cord Blood and Fetal Tissues Fetal tissue (16–22 weeks of gestation) and cord blood were obtained from ABR (Advanced Bioscience Resources Inc., ABR, Alameda, Calif.). Mononuclear cells (MNC) were isolated from these samples by Ficoll density gradient centrifugation (Lymphoprep, 1.077 g/ml, Amersham Pharmacia Biotech Inc., Piscataway, N.J.). MNC were washed three times in phosphate buffered saline (PBS; BioWhittaker Inc., Walkersville, Md.), and resuspended in PBS containing 2% (vol./vol.) human serum (HS) (Gemini Bioproducts, Woodland, Calif.) and 2 mM EDTA (PBS/HS/EDTA). Magnetic bead depletion was performed to remove lineage positive cells. Briefly, mononuclear cells were incubated with a mixture of antibodies against CD3 (OKT-3 ascites), CD8 (OKT-8 ascites), CD14 (RPA-M1 ascites), CD16 (3G8) (Immunotech, Miami, Fla.), CD19 (4G7 ascites), CD56 (My31 ascites), CD66B (80H3) (Immunotech), and Glycophorin A (10F7MN ascites). After two washes the cells were incubated with goat-anti-mouse IgG coupled to magnetic beads (Dynabeads® M-450, goat-anti-mouse IgG; Dynal Inc., Lake Success, N.Y.) and isolated according to the manufacturer's instructions. The enriched cells were stained either to perform a four-color flow cytometric analysis or to purify different subsets by cell sorting (FACS®; Beckton Dickinson, San Jose, Calif.). Cells were incubated with a cocktail of the following FITC-conjugated antibodies: CD3 (Leu-4), CD14 (Leu-M3), CD15 (Leu-M1), CD16 (Leu-11a), CD20 (Leu-16), CD57 (Leu-7) (Beckton Dickinson), and CD11c (3.9) (Caltag Laboratories, Burlingame, Calif.). To analyze expression of different antigens on the lineage FITC-negative cells the cells were stained with CD34-APC (HPCA-2) (Beckton Dickinson) and CD45RA-TRICOLOR (MEM 56) (Caltag), and in addition different PE-conjugated antibodies: anti-HLA-DR (Beckton Dickinson), CD4 (Leu-3a) (Beckton Dickinson), IL-3Rα (9F5) (PharMingen, San Diego, Calif.). For cell sorting the enriched cells were stained with CD34-APC (HPCA-2), CD45RA-PE (Leu-18), and CD4-biotin (Leu-3a) from Beckton Dickinson. Expression of CD4 was revealed after a second step staining using the streptavidin-alexa594 (Molecular Probes, Eugene, Oreg.) or avidin-Texas Red (Pharmingen) conjugate.

Expression of CD34 and CD45RA on lineage negative cells reveals four different subpopulations. Lineage positive cells (including T, B, NK cells, monocytes, granulocytes, erythrocytes) were depleted using magnetic beads. The enriched cells were analyzed by four-color flow cytometric analysis after staining with a FITC-conjugated cocktail of antibodies against lineage markers (including CD3, CD11c, CD14, CD15, CD16, CD20, CD57), anti-CD34-APC, anti-CD45RA-TRICOLOR, and the PE-conjugated antibodies anti-CD4 and anti-IL-3Rα. After electronic gating on FITC-negative cells, four populations of cells (A, B, C and D) were identified: population A, $CD34^{++}CD45RA^-$; population B, $CD34^{++}CD45RA^+$; population C, $CD34^+CD45RA^+$; population D, $CD34^-CD45RA^+$. Cells in population A–D were electronically gated and analyzed for expression of CD4 and IL-3Rα.

III. Cytospin and Giemsa Staining

Cytospin preparations (50,000 cells/slide) were made and after airdrying fixed in methanol (10 min). Cells were stained with Giemsa stain (Sigma Diagnostics, St. Louis, Mo.) for 20 min according to the manufacturer's instructions.

IV. RT-PCR

Total RNA was isolated from freshly sorted pre-DC2 and pro-DC2 using the guanidinium extraction method (Chomczynski and Sacchi (1987) *Anal. Biochem.* 162:156–159) and reverse transcribed for 1 hour at 42° C. using 200 U Moloney Murine Leukemia Virus (Superscript II, Gibco-BRL), both random (50 ng/reaction, Pharmacia), and oligo(dT)12–18 primers (500 ng/reaction, Pharmacia) according to the manufacturer's instructions. The cDNA was used as a template in the PCR reactions using primers specifically amplifying the β-actin cDNA, which served as the internal control for the amount of cDNA used per reaction, and the pre-TCR alpha cDNA. Each PCR cycle consisted of 30 sec at 94° C., 30 sec at 60° C., and 1 min at 72° C. Samples were taken after 28, 31, and 34 cycles and run on a 2% agarose gel. Marker VI (Boeringer Mannheim, Indianapolis, Minn.) was used to determine the size of the PCR products. The Mactin PCR generated a 838 bp product, and the pre-TCR alpha PCR a 374 bp product.

Appropriate primers used were for: pre-TCR alpha-sense; pre-TCR alpha-antisense; β-actin sense; and β-actin antisense.

V. DC2 Culture Conditions

For generation of DC2, sorted cells were cultured for 5 days in the presence of IL-3 (10 ng/ml, R&D Systems Inc., Minneapolis, Minn.) and CD40-Ligand transfected L cells (10,000/well, irradiated 7000 rad) in 25 μl Yssel's medium (Yssel, et al. (1984) *J. Immunol. Methods* 72:219–227) containing 2% HS in microwell plates (Robbins Scientific Corporation, Sunnyvale, Calif.).

VI. Proliferation Assay

Sorted cells (15,000/well) were cultured in duplicate for the indicated duration's in the presence of IL-3 (10 ng/ml, R&D Systems), GM-CSF (800 U/ml, a gift from Schering-Plough, N.J.), FLT3-Ligand (100 ng/ml, a gift from S. Menon, DNAX), and SCF (10 ng/ml, R&D Systems) in 200 μl Yssel's medium (Yssel, et al. (1984) *J. Immunol. Methods* 72:219–227) containing 2% HS in 96-well round bottomed culture plates (Falcon®, Beckton Dickinson). $^3$H-Thymidine (1 μCi/well; Amersham Life Science) was added during the last 8 h of the culture.

VII. IFN-α Production

Cells ($10^6$/ml) were cultured in 25 μl Yssel's medium containing 2% HS in microwell plates (Robbins Scientific). Herpes simplex virus-1 (HSV-1, KOS strain, attenuated by γ-irradiation; a gift from R. Chase, Schering-Plough, N.J.) was added at 10 pfu per cell. After 24 hours supernatants were collected and frozen at −20° C. before analysis by an IFN-α specific sandwich ELISA (Biosource International, Camarillo, Calif.). Appropriate dilutions of the supernatants were made if necessary. Production levels for the IPC typically run in the 5000–70,000 pg per 20,000 cells, but there exists certain variations according to individual and other factors.

VIII. pre-DC2/IPC Generation from Stem Cells

Sorted cells (25,000–50,000/well) were cultured in 200 μl Yssel's medium containing 2% HS in 96-well round-bottomed culture plates. Cytokines were added at the following concentrations: FLT3-Ligand (100 ng/ml, kindly provided by S. Menon, DNAX), GM-CSF (800 U/ml, a gift from Schering Plough), SCF (10 ng/ml, R&D Systems), IL-3 (10 ng/ml, R&D Systems), IL-7 (10 ng/ml R&D Systems), G-CSF (5 ng/ml, R&D Systems). Cell cultures were refreshed every 5 days by demi-depletion and splitted if necessary.

IX. Identification of Pro-DC2, the CD34 Expressing Immediate Precursors of pre-DC2/IPC Pre-DC2/IPC have been identified in tonsil, adult peripheral blood (see Rissoan, et al. (1999) *Science* 283:1183–1186; and Grouard, et al. (1997) *J. Exp. Med.* 185:1101–1111), and postnatal thymus (see Res, et al. (1999) *Blood* 94:2647–2657). To define the developmental pathway of pre-DC2/IPC from CD34$^{++}$ heamatopoietic progenitors, lineage positive cells (including T, B, NK cells, monocytes, granulocytes, erythrocytes) from fetal liver, bone marrow, cord blood, and adult blood were depleted using magnetic beads. The remaining lineage negative cells were analyzed by four-color flow cytometry analysis after staining with: i) FITC-conjugated antibodies against lineage markers (CD3, CD11c, CD14, CD15, CD16, CD20, CD57), in order to exclude the remaining lineage$^+$ cells; ii) anti-CD34 antibody conjugated to APC, to follow the populations of heamatopoietic progenitor cells; iii) anti-CD45RA antibody conjugated to TRICOLOR, as a positive marker to identify pre-DC2/IPCs and to distinguish CD34$^{++}$CD45RA$^-$ early progenitors from CD34$^{++}$CD45RA$^+$ late progenitors; and iv) various PE-conjugated antibodies known to detect antigens expressed on pre-DC2/IPCs, such as CD4 and IL-3R$\alpha$. After gating on FITC-negative cells, four populations of cells (A, B, C and D) were identified. CD34$^{++}$CD45RA$^-$ cells (population A) are enriched for early multipotent progenitor cells (see Fritsch, et al. (1995) *Ann. N.Y. Acad. Sci.* 770:42–52), while CD34$^{++}$CD45RA$^+$ cells (population B) are enriched for myeloid/lymphoid progenitors, which have lost the potential to develop into the erythroid lineage (see Galy, et al. (1995) *Immunity* 3:459–473). These two populations of CD34$^{++}$ progenitor cells expressed lower levels of CD4 and IL-3R$\alpha$ than expressed by pre-DC2/IPCs derived from adult peripheral blood or tonsils. A substantial proportion of CD34$^+$CD45RA$^+$ cells in population C and CD34$^-$CD45RA$^+$ cells in population D expressed a moderate level of CD4 and a high level of IL-3R$\alpha$, similar to the expression level detected on pre-DC2/IPCs from adult peripheral blood or tonsils. The CD4$^-$ and IL-3R$\alpha^-$ fraction of cells in populations C and D expressed NKRP1A, and most likely represent cells of the NK lineage (see Lanier, et al. (1994) *J. Immunol.* 153:2417–2428). Thus, according to these phenotypical analyses, the CD34$^-$CD45RA$^+$CD4$^+$IL-3R$\alpha^{++}$ cells in population D may represent pre-DC2/IPCs. Furthermore, because of the low CD34 expression, the CD34$^+$CD45RA$^+$CD4$^+$IL-3R$\alpha^{++}$ cells in population C may represent the immediate progenitors of pre-DC2/IPCs. Accordingly, the CD34$^+$CD45RA$^+$CD4$^+$IL-3R$\alpha^{++}$ cells in population C will be referred to as pro-DC2 (for progenitor of pre-DC2). The presence of pro-DC2 could be detected in cord blood, fetal bone marrow, fetal liver, and at very low numbers in peripheral blood, but not in fetal thymus. All tissues analyzed contained pre-DC2 in population D.

X. Pro-DC2 and Pre-DC2 Produce Large Amounts of IFN-$\alpha$ After Viral Stimulation A key function feature of pre-DC2/IPCs is the rapid production of huge amounts of IFN-$\alpha$/$\beta$ in response to viral stimulation. see, e.g., Kadowaki, et al. (2000) *J. Exp. Med.* 192:219–226; and Siegal, et al. (1999) *Science* 284:1835–1837. To determine if CD34$^+$ pro-DC2s in population C have acquired this function, pro-DC2 were stimulated with irradiated HSV-1 (10 pfu/cell) for 24 h, in parallel with pre-DC2 and CD34$^{++}$ progenitor cell populations A and B. CD34$^{++}$CD45RA$^-$ (population A) isolated from either cord blood or fetal liver only produced low levels of IFN-$\alpha$ (A: <17–111 pg/ml, n=11) (Table I). Similar low IFN-$\alpha$ levels were found for virally stimulated cord blood CD34$^{++}$CD45RA$^+$ (population B) cells (B: 17–48 pg/ml, n=4). However, the range of IFN-$\alpha$ production from fetal liver derived CD34$^{++}$CD45RA$^+$ cells was more variable (B: <17–4,257 pg/ml, n=11). Pro-DC2 in population C and pre-DC2 in population D isolated from either cord blood or fetal liver produced huge amounts of IFN-$\alpha$ (pro-DC2: 172–90,464 pg/ml, n=10; pre-DC2: 1,024–15,830 pg/ml, n=8) (Table 1). No IFN-$\alpha$ was detectable from the CD4$^-$ cells in population D after purification and viral stimulation, suggesting that these cells are different from the pre-DC2.

TABLE 1

IFN-$\alpha$ producing capacity of purified pro-DC2, pre-DC2, and CD34++ progenitor subsets from cord blood and fetal liver.

| | CD34$^{++}$CD45RA$^-$ | CD34$^{++}$CD45RA$^+$ | pro-DC2 | pre-DC2 |
|---|---|---|---|---|
| cord blood | | | | |
| 1 | 32 | 36 | 4295 | 3254 |
| 2 | 41 | 48 | 172 | 1024 |
| 3 | 43 | 43 | 6938 | 13020 |
| 4 | — | — | 1284 | 3484 |
| 5 | — | — | 10835 | 9241 |
| 6 | 20 | 17 | — | — |
| fetal liver | | | | |
| 1 | <17 | 1270 | 90464 | — |
| 2 | 76 | 1241 | 39577 | 15830 |
| 3 | 111 | 41 | 20308 | 900 |
| 4 | 81 | 1496 | 26662 | 9847 |
| 5 | 32 | 4257 | 90010 | — |
| 6 | 23 | 46 | — | — |
| 7 | <17 | <17 | — | — |

CD34++ progenitor subsets, pro-DC2, and pre-DC2 were purified by flow cytometric cell sorting and stimulated with HSV-1 for 24 h. The amount of IFN-$\alpha$ (pg/ml) produced in supernatants was measured by ELISA. The threshold detection by ELISA was about 17 pg/ml.
— not tested.

These data indicate that pre-DC2s from fetal liver and cord blood are similar to pre-DC2/IPCs isolated from adult blood and tonsils regarding their surface phenotype and function in anti-viral innate immunity. Furthermore, although pro-DC2 express the CD34 antigen, these cells already acquired the functional capacity to produce a large amount of IFN-$\alpha$ in response to viral stimulation and therefore pro-DC2 may represent the earliest IPCs during heamatopoiesis. In addition, the ability to rapidly produce vast amounts of type-1 IFN is acquired during heamatopoietic development, since CD34$^{++}$ early heamatopoietic progenitors only produced a low amount of IFN-$\alpha$ in response to viral stimulation.

XI. Pro-DC2s display plasmacytoid morphology

Freshly sorted pre-DC2 display a plasma cell-like morphology, characterized by an eccentric nucleus, a blue basophilic cytoplasm and pale Golgi zone. Grouard, et al. (1997) *J. Exp. Med.* 185:1101–1111. To determine the morphology of pro-DC2, Giemsa staining of the freshly isolated pro-DC2 from fetal liver was done in parallel with freshly isolated pre-DC2 from adult blood. Pro-DC2s revealed a morphology and a high cytoplasmic content, which was very similar to pre-DC2s.

XII. Pro-DC2s Express Transcripts for pre-TCR Alpha

During T cell development in the thymus, early T cells express a pre-TCR complex, consisting of a TCR$\beta$, protein and the chaperone pre-TCR alpha chain. von Boehmer and Fehling (1997) Annu. Rev. Immunol. 15:433–452. Recent studies demonstrated that pre-DC2 from peripheral blood, tonsil, and postnatal thymus also expressed mRNA for the pre-TCR alpha chain, suggesting that pre-DC2 may be of lymphoid lineage. Res, et al. (1999) Blood 94:2647–2657; and Bruno, et al. (1997) J. Exp. Med. 185:875–884. To determine whether pro-DC2 expressed the pre-TCR alpha chain mRNA, semi-quantitative RT-PCR using pre-TCR alpha specific primers was performed on RNA isolated from purified pro-DC2 and pre-DC2. Pre-TCR alpha transcripts could be detected in pro-DC2, although the level of expression was 8-fold lower compared to pre-DC2. These data support the notion that pro-DC2 are the immediate progenitor cells of pre-DC2 and are of lymphoid origin.

XIII. Pro-DC2s differentiate into mature dendritic cells upon IL-3 and CD40-Ligand stimulation Adult blood and tonsil-derived pre-DC2 depend on IL-3 for their survival. Grouard, et al. (1997) J. Exp. Med. 185:1101–1111. Culture of pre-DC2 with IL-3 and CD40-Ligand transfected L cells results in their differentiation into mature dendritic cells (DC2). Grouard, et al. (1997) J. Exp. Med. 185:1101–1111; and Rissoan, et al. (1999) Science 283:1183–1186. To determine whether pro-DC2 have the potential to differentiate into mature DCs, the cells were cultured for 5 days with IL-3 and CD40L-Ligand in parallel with pre-DC2s. After 5 days of culture, both pro-DC2 and pre-DC2 acquired mature DC morphology. Moreover, flow cytometry analysis revealed that both cultured pro-DC2 and pre-DC2 expressed mature DC markers, such as high HLA-DR, CD80, CD86, CD40, and CD83. These results suggest that pro-DC2 and pre-DC2 have an equal potential to develop into mature dendritic cells.

XIV. Pro-DC2 Have a Limited Proliferative Capacity

The proliferation potential of pro-DC2 in response to heamatopoietic cytokines was analyzed, in parallel with that of pre-DC2, CD34$^{++}$CD45RA$^-$ (population A) and CD34$^{++}$CD45RA$^+$ (population B) from fetal liver. Cells of each population were cultured for a total of 5 days in a cytokine cocktail consisting of GM-CSF, IL-3, SCF, and FLT3-Ligand. [3H]-Thymidine was added to the cultures 8 h before incorporation was analyzed. Pro-DC2 proliferated moderately better than pre-DC2, but 50–100 times less than CD34++CD45RA– (population A) and CD34+CD45RA+ (population B). In addition, both pro-DC2 and pre-DC2 failed to undergo clonal expansion in these cultures.

These data suggest that although pro-DC2 still express the CD34 antigen and proliferate moderately better in response to cytokines than pre-DC2, the pro-DC2 may have lost the clonal expansion potential of heamatopoietic progenitor cells.

XV. FLT3-Ligand Induces CD34++CD45RA– Early Heamatopoietic Progenitor Cells to Differentiate into IFN-__ Producing Cells CD34++CD45RA– cells did not produce IFN-__ after viral stimulation, but were found to have the best clonal expansion potential. It was investigated whether CD34++CD45RA– early progenitor cells can be induced to differentiate into pre-DC2/IPCs in vitro with one of the following cytokines: IL-3, IL-7, SCF, FLT3-Ligand, GM-CSF, or G-CSF. After 11 and 25 days of culture, 20,000 cells were stimulated with HSV-1 for 24 hours and the amount of IFN-__ secreted in the supernatants was analyzed by ELISA. At day 11, cells cultured with FLT3-Ligand or SCF produced moderate levels of IFN-__ (FLT3-Ligand: 3,323 pg/ml, SCF: 2,910 pg/ml) after viral stimulation. Cells cultured in any of the other cytokines produced low to undetectable levels of IFN-__ (<17–24 pg/ml). The cells expanded in number up to 35 fold with IL-3 and 24 fold with GM-CSF, while the cell number expansion with the other cytokines was less than 5-fold. Strikingly, after 25 days of culture with FLT-3-Ligand, CD34++CD45RA– cells produced 15,794 pg/ml of IFN-__ after viral stimulation. Interestingly, the capacity of cells to produce IFN-__ after culture in SCF had decreased to 767 pg/ml. Cellular expansion in this experiment was about 24-fold in FLT3-Ligand and 6-fold in SCF. None of the other cytokines had induced the CD34+CD45RA– cells to produce IFN-__ upon viral challenge.

To analyze the detailed kinetics of the capacity of FLT3-Ligand cultured cells to produce IFN-α in response to HSV-1 stimulation, CD34$^{++}$CD45RA$^-$ fetal liver cells were cultured in FLT3-Ligand and harvested every 5 days. After 10–15 days of culture, CD34$^{++}$CD45RA$^-$ early progenitor cells acquired the capacity to produce significant amounts of IFN-α (3,000–5,000 pg/ml). This capacity was further increased at day 21 (20,000 pg/ml), peaked at day 25 to day 30 (>58,000 pg/ml), and started to decrease after 50 days of culture. The cell number of CD34$^{++}$CD45RA$^-$ cells cultured in FLT3-Ligand increased about 6–7 fold after 4 weeks of culture.

XVI. FLT3-Ligand Induces CD34$^{++}$CD45RA$^-$ Early Progenitor Cells to Differentiate into CD4$^+$HLA-DR$^+$IL-3Rα$^{++}$CD45RA$^+$CD11c$^-$ pre-DC2.

Four-color flow cytometry was used to determine whether the production of the vast amounts of IFN-α by FLT3-Ligand cultured cells was due to the generation of pre-DC2/IPCs. In normal human adult blood, the frequency of CD4$^+$HLA-DR$^+$IL-3Rα$^{++}$CD45RA$^+$CD11c$^-$ pre-DC2s is between 0.3–0.8% of total peripheral blood mononuclear cells. Grouard, et al. (1997) J. Exp. Med. 185:1101–1111. The percentage of CD4$^+$HLA-DR$^+$IL-3Rα$^{++}$CD45RA$^+$CD11c$^-$ cells in freshly isolated CD34$^{++}$CD45RA$^-$ early progenitor cells from fetal liver or in 5 days FLT3-Ligand cultured cells was less than about 0.05%. A progressive increase (from about 1.5% to 6%) in the percentage of HLA-DR$^+$IL-3Rα$^{++}$ cells was observed from day 11 to day 20 of culture. Between day 25 and day 30, up to 10% of the cultured cells were HLA-DR$^+$IL-3Rα$^{++}$ cells. Detailed flow cytometric analysis of CD34$^{++}$CD45RA$^-$ cells at day 30 of FLT3-Ligand culture revealed that the HLA-DR$^+$IL-3Rα$^{++}$ cells expressed CD4, CD45RA, and low levels of CD11c, a typical phenotype of pre-DC2/IPC. Most interestingly, a clear correlation was observed between the ability of cultured cells to produce large amounts of IFN-α in response to viral stimulation and the appearance of CD4$^+$HLA-DR$^+$IL-3Rα$^{++}$CD45RA$^+$CD11c$^-$ cells in culture with FLT3-Ligand.

To directly show that the IL-3Rα$^{++}$HLA-DR$^+$ cells generated from CD34$^{++}$CD45RA$^-$ early progenitor cells with FLT3-Ligand were pre-DC2/IPCs, FLT3-Ligand cultured cells were separated into IL-3Rα$^{++}$HLA-DR$^+$ and IL-3Rα$^{low}$HLA-DR$^+$ populations by cell sorting. Stimulation of sorted cells with HSV-1 for 24 hours revealed that the IL-3Rα$^{++}$HLA-DR$^+$ produced the larger amount of IFN-α (about 50,000 pg/ml), which was 7 times more than produced by the IL-3Rα$^{low}$HLA-DR$^+$ (about 7,000 pg/ml). Notably, the amount of IFN-α produced by these in vitro generated cells is comparable to that produced by freshly isolated IPC from fetal liver. See Table 1.

These data indicate that pre-DC2/IPCs were generated from CD34$^{++}$CD45RA$^-$ early heamatopoietic progenitor cells in culture with FLT3-Ligand.

XVIII. Other Heamatopoietic Cytokines do not Promote the FLT3-Ligand Induced Generation of pre-DC2/IPC from CD34$^{++}$CD45RA$^-$ Early Progenitor Cells The possibility was tested whether the FLT3-Ligand induced generation of pre-DC2/IPC could be enhanced by addition of other cytokines, e.g., GM-CSF, G-CSF, IL-3, IL-7, and SCF to the culture. Although G-CSF and, to a lesser extent, GM-CSF and SCF significantly enhanced the clonal expansion of CD34$^{++}$CD45RA$^-$ cells after 25 days of cultures, none of the tested cytokines promoted either the generation of pre-DC2/IPCs as determined by IFN-α/β production in response to viral stimulation or by the percentage of cells expressing the pre-DC2/IPCs phenotype (CD4$^+$HLA-DR$^+$IL-3Rα$^{++}$CD45RA$^+$CD11c$^-$). Moreover, the tested cytokines, in particular IL-3 inhibited the generation of pre-DC2/IPCs induced by FLT3-Ligand.

The evolutionary pressure to fight numerous types of microorganisms has endowed us with the development of not only the sophisticated adaptive immune system including T and B lymphocytes, but also the divine innate immune system. While neutrophils and macrophages are dedicated to eat and kill various bacteria, the eosinophils, basophils, and mast cells have evolved to kill parasites. The robust production of IFN-α/β of pre-DC2/IPCs in response to viral stimulation suggests that pre-DC2/IPCs represent a new member cell type of the heamatopoietic family and an effector cell type of the innate immune system against anti-viral infection.

Haematopoietic stem cells develop into committed effector cells depending on their microenvironment, which provides them with the necessary stimuli. This development is a multi-step process that requires the orchestrated availability of cytokines and chemokines in order for the cells to proliferate, differentiate, and migrate accurately. The present invention establishes a developmental pathway of pre-DC2/IPCs from CD34$^{++}$CD45RA$^-$ early progenitors, to CD34$^{++}$CD45RA$^+$ late progenitors, to CD34$^+$CD45RA$^{++}$IL-3Rα$^{++}$CD4$^+$HLA-DR$^+$CD11 c$^-$ pro-DC2, and finally to CD34$^-$CD45RA$^+$IL-3Rα$^{++}$CD4$^+$HLA-DR$^+$CD11c$^-$ pre-DC2/IPCs. The expression of pre-TCR alpha chain transcripts in pro-DC2 and pre-DC2 supports the concept that pre-DC2/IPCs are of lymphoid lineage. This differentiation pathway may provide a basis to further study the function and development of pre-DC2 in normal and disease states. For example, it was recently reported that both G-CSF and FLT-3-Ligand treatment of healthy donors increased pre-DC2 numbers in the peripheral blood. The present study provides a model to study the effects of both cytokines on the different developmental stages of pre-DC2 in vivo. Furthermore, it has been reported that there is a progressive loss of the IFN-α/β producing capacity of peripheral blood cells in response to viral stimulation in patients with hairy cell leukemia, steroid treatment, idiopathic CD4 lymphopenia, and HIV. See Fitzgerald-Bocarsly (1993) *Pharmacol. Ther.* 60:39–62. It will be important to determine the stage where pre-DC2 development and function is disturbed in these patients in order to anticipate clinical treatment.

These studies also demonstrate the generation of pre-DC2/IPCs in vitro from CD34$^{++}$CD45RA$^-$ early heamatopoietic progenitor cells with FLT3-Ligand. The generated cells not only had the capacity to produce huge amounts of IFN-α/β in response to viral stimulation, but also displayed a typical pre-DC2/IPC phenotype of CD4$^+$IL-3Rα$^{++}$CD45RA$^+$HLADR$^+$CD11c$^-$. Notably, the finding that neither pro-DC2 nor pre-DC2 could survive and proliferate in culture with FLT3-Ligand indicates that the presence of pre-DC2/IPCs was due to their differentiation from CD34$^{++}$CD45RA$^-$ early progenitor cells, and not the selective expansion of contaminating pro-DC2s or pre-DC2s. Injection of FLT3-Ligand was previously shown to dramatically increase the numbers of both myeloid and lymphoid DC in blood and lymphoid tissues of mice. Maraskovsky, et al. (1996) *J. Exp. Med.* 184:1953–1962; and Shurin, et al. (1997) *Cell Immunol.* 179:174–184. A recent study by Pulendran, et al. (2000) *J. Immunol.* 165:566–572 showed that FLT3-Ligand treatment also increased the number of both CD11c$^+$ myeloid DCs and CD4$^+$IL-3Rα$^{++}$CD11c$^-$ pre-DC2/IPCs in peripheral blood of human donors. Those findings, together with this study, suggest that FLT3-Ligand directly induces the differentiation of a proportion of CD34$^{++}$CD45RA$^-$ early progenitor cells into pre-DC2/IPCs. Whether FLT3-Ligand promotes the migration of pre-DC2 generated in bone marrow into the blood circulation remains unknown. Two recent studies showed that in G-CSF treated patients or stem cell donors, the number of pre-DC2 in blood was increased 5-fold, while the number of CD11c$^+$ DC was not affected. Arpinati, et al. (2000) *Blood* 95:2484–2490; and Pulendran, et al. (2000) *J. Immunol.* 165:566–572. The current finding that G-CSF was unable to induce CD34$^{++}$CD45RA$^-$ early progenitor cells to differentiate into pre-DC2/IPCs suggests that unlike FLT3-Ligand, G-CSF did not support differentiation of early heamatopoietic progenitor cells into pre-DC2/IPCs, but may promote the migration of pre-DC2 into peripheral blood.

IFN-α/β has been widely used in treating patients with viral hepatitis. Reusser (2000) *Schweiz Med. Wochenschr* 130:101–112. Potentially, combination therapy of IFN-α/β and FLT3-Ligand or G-CSF can be used to increase the number of pre-DC2/IPCs to treat patients with chronic viral infection. Several studies suggest that in HIV infected patients, there is a progressive loss of the ability of blood leukocytes to produce IFN-α/β in response to viral infections. Siegal, et al. (1986) *J. Clin. Invest.* 78:115–123; Fitzgerald-Bocarsly, et al. (1989) *J. Infect. Dis.* 160:1084–1085; and Rossol, et al. (1989) *J. Infect. Dis.* 159:815–821. Pre-DC2/IPCs express CD4 and chemokine receptors CXCR4 and CCR5, which are the receptors allowing HIV entry. Baiter (1996) *Science* 272:1740; and Deng, et al. (1996) *Nature* 381:661–666. We have recently observed that there is a dramatic decrease in pre-DC2/IPC numbers in HIV infected patients with AIDS, in particular in AIDS patients with complication of infections and of Kaposi Sarcoma. While it remains to be established whether pre-DC2/IPCs are infected by HIV viruses, FLT3-Ligand together with the therapies preventing HIV infection should be beneficial for patients to ultimately eliminate viruses.

The present study has mapped the pathways and identified the cytokine regulation of pre-DC2/IPCs development from early heamatopoietic stem cells in humans. The pre-DC2/IPC developmental pathway will provide a basis for monitoring pre-DC2/IPCs numbers and development in patients with tumors and autoimmune and infectious diseases. FLT-3-Ligand and G-CSF have the potential to be used to stimulate the generation and mobilization of pre-DC2/IPCs in patients who are fighting against cancers and infectious diseases.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A method of producing IPC comprising contacting CD34++CD45RA-early heamatopoietic progenitor cells for at least 13 days with an effective amount of a combination of FLT3-Ligand and TPO wherein: (a) the progenitor cells accumulate within 24 hrs, at least 5000 pg IFN per 20,000 IPC after viral stimulation; and (b) the IPC number at least $1 \times 10^7$.

2. The method of claim 1, wherein the contacting is for at least 19 days.

3. The method of claim 1, wherein the contacting is for at least 23 days.

4. The method of claim 1, wherein the effective amount of FLT3-Ligand is 100 ng/ml and TPO is 100 ng/ml.

5. The method of claim 1, wherein the amount of IFN produced by the progenitor cells Is between at least 5000–70,000 pg per 20,000 cells.

6. The method of claim 1, wherein HSV-1 is the viral stimulation.

7. The method of claim 1, wherein the progenitor cells are from fetal liver or cord blood.

* * * * *